United States Patent [19]
Ofstead

[11] Patent Number: 4,859,719
[45] Date of Patent: Aug. 22, 1989

[54] POLYMER BLENDS WITH HIGH WATER ABSORPTION

[75] Inventor: Ronald F. Ofstead, St. Paul, Minn.

[73] Assignee: Minnesota Mining and Manufacturing Company, St. Paul, Minn.

[21] Appl. No.: 205,675

[22] Filed: Jun. 13, 1988

Related U.S. Application Data

[60] Division of Ser. No. 753,406, Jul. 10, 1985, Pat. No. 4,771,089, which is a continuation-in-part of Ser. No. 530,199, Sep. 8, 1983, abandoned.

[51] Int. Cl.$^4$ .......................... G02C 7/02; G02C 7/04
[52] U.S. Cl. .................... 523/108; 523/105; 523/106; 264/319; 351/159; 351/160 R; 351/160 H
[58] Field of Search ............... 523/106, 108; 525/133; 350/409, 417; 264/319; 351/161 H, 161 R; 106/105

[56] References Cited

U.S. PATENT DOCUMENTS

| | | | |
|---|---|---|---|
| 3,287,441 | 11/1966 | Magat | 260/857 |
| 3,798,289 | 3/1974 | McGrath et al. | 260/895 |
| 3,816,571 | 6/1974 | O'Driscoll et al. | 264/1 |
| 3,949,021 | 4/1976 | Kunitomo et al. | 260/895 |
| 4,067,839 | 1/1978 | Schultz | 260/29.6 |
| 4,123,408 | 10/1978 | Gordon | 260/29.6 |
| 4,130,517 | 12/1978 | Lundberg et al. | 260/878 |
| 4,279,795 | 7/1981 | Yamashita et al. | 525/301 |
| 4,300,820 | 11/1981 | Shah | 351/160 |
| 4,361,689 | 11/1982 | Patel et al. | 526/264 |
| 4,379,893 | 4/1983 | O'Malley et al. | 525/386 |
| 4,388,428 | 6/1983 | Kuzma et al. | 523/106 |
| 4,451,629 | 5/1984 | Tanaka et al. | 526/238.23 |

FOREIGN PATENT DOCUMENTS 825548 5/1981 U.S.S.R. .

OTHER PUBLICATIONS

American Heritage Dictionary, New College Edition, 1976, p. 187.
Webster's New Collegiate Dictionary, 1978, p. 117.
American Heritage Dictionary, New College Edition, 1976, p. 805.
Principals of Polymer Chemistry, p. 47. (date unavailable).
Yamashita et al., pp. 187–195, (date unavailable).
S. Krause, Journal of Macromolecular Science, Reviews of Macromolecular Chemistry, C7, 251 (1972).
D. R. Paul (ed.) "Polymer Blends", vol. 1, pp. 15–113, Academic Press, New York, 1978.
O. Olabisi, L. M. Robeson and M. T. Shaw, "Polymer-polymer Miscibility", pp. 115–276, Academic Press, New York, 1979.
J. Appl. Science, 9, 1385 (1965).
J. Colloid Interface Sci. 31, 168 (1969).
Nippon Setchaku Kyokai Shi, 11, 2 (1975).
Polymer Prep., Amer. Chem. Soc. Div. Polymer Chem. 10, 385 (1969).

*Primary Examiner*—Allan M. Lieberman
*Attorney, Agent, or Firm*—Donald M. Sell; Walter N. Kirn; James V. Lilly

[57] ABSTRACT

Miscible blends of slid, non-crosslinked polymers are disclosed. The blends comprise from 2 to 95 parts by weight of a water-insoluble, hydrophobic polymer and, correspondingly from 98 to 5 parts by weight of a hydrophilic polymer. The blends are capable of absorbing at least their own weight in water.

13 Claims, No Drawings

POLYMER BLENDS WITH HIGH WATER ABSORPTION

Cross Reference to Related Application

This is a division of application Ser. No. 753,406 filed July 10, 1985 and now U.S. Pat. 4,771,089, which is a continuation in-part of application Ser. No. 530,199 filed Sept. 8, 1983 now abandoned.

TECHNICAL FIELD

The present invention relates to blends of solid, non-crosslinked polymers capable of absorbing a sufficient quantity of water to provide a composition comprising at least 50% by weight water. It further relates to processes for the preparation of such blends and to articles, such as contact lenses, prepared from such blends. The blends of the invention may also be employed in a variety of other ways including, for example, as shaped articles, membranes, composites, sealants, gels, and the like.

As it is used herein, the phrases "miscible polymer blends" and "miscible blends" mean a composition of two or more polymer components in which the separate components are no longer separately distinguishable yet are present as individual components.

BACKGROUND ART

Mixtures of polymers have been previously described which are said to be miscible within certain temperature ranges and/or in certain polymer ratios. However, the overwhelming majority of polymers employed in mixtures are immiscible in each other. Furthermore, unless there is direct evidence showing miscibility, all mixtures of polymers should be presumed to be immiscible. Relevant reviews of the subject of polymer miscibility include S. Krause, Journal of Macromolecular Science, Reviews of Macromolecular Chemistry, C7, 251 (1972); D. R. Paul (ed.) "Polymer Blends", Volume 1, pp. 15-113, Academic Press, New York, 1978; and O. Olabisi, L. M. Robeson and M. T. Shaw, "Polymer-polymer Miscibility", pp. 215-276, Academic Press, New York, 1979.

Polymer mixtures have also been described in various other publications. For example, U.S. Pat. No. 3,949,021 discloses solutions of water-insoluble polymers and cross-linking agents in monomeric N-vinylpyrrolidone which are polymerized to provide hard, solid materials which may be machined, cut and/or polished. These materials are crosslinked hydrogels which are said to be suitable for extended-wear contact lenses. However, the crosslinked nature of such materials causes them to lose their thermoplasticity.

U.S. Pat. No. 4,300,820 discloses compositions of N-vinylpyrrolidone with water-insoluble copolymers. Ethylenically unsaturated monomers which contain acid groups are included in the coompositions. However, such compositions do not form miscible blends as that term is defined herein.

U.S. Pat. No. 3,287,411 discloses mixtures of a poly(N-vinyl amide) and a polymer from the group of polyamides, polyureas and polyurethanes. The mixtures are said to be homogeneous.

U.S. Pat. No. 3,798,289 discloses that mixtures of polyvinyl chloride and a copolymer of N,N-dimethylacrylamide and ethylene are miscible at a 1:1 ratio. However, such mixtures are incapable of absorbing sufficient water to provide compositions containing more than 50% by weight water due to the high level of hydrophobic polyvinyl chloride in the composition.

Other mixtures of polymers are disclosed in J. Appl. Polymer Science, 9, 1385 (1965). These mixtures include polyethylene oxide and polyvinylnaphthalene. This mixture is compatible only when more than 45 weight % polyvinylnaphthalene is present. However, such a high level of a hydrophobic material renders the mixture incapable of providing compositions having more than 50% by weight water.

U.S. Pat. No. 4,279,794 discloses graft copolymers wherein hydrophobic branches are covalently grafted to hydrophilic backbones. These polymers form immiscible "seas" and "islands". The seas typically comprise the hydrophilic phase while the islands typically comprise the hydrophobic phase. See S. Yamashita, K. Shibatani, K. Takakura and K. Imai, "Reinforced Biocompatible Hydrogel", Kobunshi Ronbunshu, 39(4), pg. 187-95.

The J. Colloid Interface Sci. 31,168 (1969) discloses a miscible blend of polyethylene oxide and polypropylene oxide. Such blends are miscible only for low molecular weight polymers in the liquid phase.

Nippon Setchaku Kyokai Shi, 11, 2(1975) discloses that copolymers of N-vinylpyrrolidone and vinyl acetate (PVNP/VA) can be mixed with other polymers to provide compositions that contain 50 weight % PVNP/VA and 50 weight % other polymer. Such blends are incapable of providing compositions containing more than 50% by weight water due to the high level of hydrophobic component.

Polymer Prep., Amer. Chem. Soc. Div. Polymer Chem. 10, 385 (1969) discloses mixtures of polyvinyl acetate and a copolymer of polymethyl vinyl ether and maleic anhydride.

DISCLOSURE OF THE INVENTION

In one aspect, the present invention is directed to a composition containing a blend of non-crosslinked polymers comprising from about 2 to 95 parts by weight of a water-insoluble, hydrophobic polymer and, correspondingly from about 98 to 5 parts by weight of a hydrophilic polymer, said composition being transparent and capable of absorbing a sufficient quantity of water to provide a material containing at least 50 weight % water.

As used herein, the following terms have the following meanings:

"Water-insoluble" means (i) less than 1% (preferably less than 0.1%) soluble in water, and (ii) absorbs less than 10% water;

"Hydrophobic" means a substance which adsorbs or absorbs essentially no water;

"Transparent" means a substance which transmits light rays so that objects on one side may be distinctly seen on the other side; neight opaque or translucent;

"Hydrophilic" means a substance which adsorbs or absorbs water without chemical degradation under ambient use conditions and includes substances which either dissolve in water or which swell in water due to the uptake of five times or more of their own weight in water;

"Xerogel" means an anhydrous polymer which swells in an aqueous media without dissolving to give a material containing a 3-dimensional network of polymer chains.

In another aspect, the present invention is directed to a process for preparing such blends.

In yet another aspect, the present invention is directed to articles prepared from such blends, especially ophthalmic devices such as contact lenses, corneal transplants, corneal implants, and intraocular lenses.

The blends of the present invention, as noted previously, contain two or more parts which cannot be separately distinguished after combination (i.e., being blended), over a wide temperature range (e.g., $-20°$ C. to about 250° C.) even though the two parts are not covalently bonded together. The blends are thermoplastic and have high water absorptivity, e.g., they can absorb 100% or more of their own weight in water. In the hydrated state, they possess good tensile strength, modulus and percent elongation.

This combination of properties is very surprising as the blends are made up of such dissimilar polymers (i.e., hydrophilic and hydrophobic). It is even more surprising that these blends are not disrupted or rendered immiscible by the addition of water, since water is a solvent for the hydrophilic component of the blends.

DETAILED DESCRIPTION

The blends of the present invention may be characterized by the following features.

The components of the blends form single phase compositions. The presence of a single phase may be indicated by several criteria such as, for example, optical clarity, a single glass transition temperature, scattering methods, ternary solution method, and so forth. See Olabisi et al, Polymer-Polymer Miscibility, Academic Press, New York, 1979 for a more detailed discussion of such criteria.

Single phase compositions are particularly useful where optical clarity is desired, such as with optical devices (e.g., contact lenses), and where strength, stability, and durability are desired. Multi-phase mixtures are undesirable in such instances because they typically cause adsorption, scattering, or distortion of incident light and because the presence of more than one phase adversely affects strength.

Preferably the presence of a single phase is verified by the results of at least two tests. For example, optical clarity, as measured by transmitted light or (preferably) phase contrast microscopy, and a single value of glass transition temperatue ($T_g$) which is distinct from the $T_g$ of either component may be utilized. $T_g$ may be measured by conventional methods such as standard differential thermal analysis on dried samples at a 30° C. per minute heating rate. The midpoint of the resulting thermal transition curve is used as the $T_g$.

The components of the blends of the invention remain as a single phase, over an extended temperature range, e.g., $-20°$ C. to 250° C., preferably including and extending beyond the extremes of the temperature range in which they will be processed, handled and used. The upper limit is necessarily at or above the temperature at which they are melt processed while the lower limit is at or below the ambient temperatures at which they will generally be used.

The polymer blends of the invention absorb a high percentage of their own weight in water. While the water absorbancy rate may vary within the scope of the invention, the blends absorb sufficient water to provide compositions comprising at least 50% by weight water.

Within the above criteria, it is necessary that the components retain their structural integrity and not separate into discrete phases when they absorb water. This property is particularly important when the blend is hydrated to form an ophthalmic device suitable for use either on the cornea or in place of the cornea. Such devices, sometimes referred to as hydrogel lenses, are typically hydrated in a normal saline solution.

The blends of the invention are melt processable, that is, they may be formed into a desired shape at elevated temperatures without degradation and, when cooled after being melt processed, will retain the shape or configuration imparted during the melt processing. Thus, the blends of the invention may be formed into a shaped article at, e.g., 190° C. to 210° C.

The blends of the invention also possess good physical properties after being hydrated to equilibrium. For example, they have good tensile strength, elongation, and modulus. Blends of the invention were found to possess tensile strengths of from 0.5 to 30 kg/cm$^2$ or more. Preferred blends exhibited tensile strengths of greater than 2 and more preferably greater than 6 kg/cm$^2$.

Percent elongation at break of the blends of the invention preferably is greater than 70%, and more preferably greater than 150%.

Modulus of elasticity of the blends of the invention is preferably greater than 5 kg/cm$^2$ and more preferably greater than 10 kg/cm$^2$.

These physical properties all represent significant improvements over known and commercially available hydrogels.

Specific areas of utility of the hydrated blends of the invention include, for example, use as ophthalmic devices, water barriers, sealants, water sorbents, electrophoresis gels, culture media, seed coatings, optical articles, corneal implants, coating for prosthetic devices, membrane films, vascular prosthetic devices, cartilage replacements, and coextruded hydrophilic composites (e.g., catheters).

The polymer blends of the invention comprise from about 2 to 95 parts by weight of a hydrophobic polymer and from about 98 to 5 parts by weight of a hydrophilic polymer. Preferably they comprise from about 5 to 30 parts by weight of the hydrophobic polymer (more preferably from about 10 to 20 parts by weight) and from about 95 to 70 parts by weight of the hydrophilic polymer (more preferably from about 90 to 80 parts by weight).

A variety of hydrophobic polymers and hydrophilic polymers are useful in the invention. It has been found that certain criteria are helpful in selecting the various polymers to be included in the blends. For example, it has been found that hydrophobic and hydrophilic polymers whose solubility parameters are closely matched will have the greatest tendency to form miscible blends. Preferably the solubility parameters of the two polymers are within 1.0 unit of each other and most preferably within 0.5 unit of each other. Techniques for determining solubility parameter are discussed in Polymer Blends, Volume I, D. R. Paul, pp. 46–47.

Other criteria which may be used to select polymers for use in the blends of the invention are the critical interaction parameter (which includes a molecular weight contribution) and the spinodal interaction parameter (which includes blend compositional contributions). These techniques are also described in Polymer Blends, Volume I, Chapter 2.

Microcalorimetry measurements of model compounds representative of the polymer structure may also be used to select specific polymers. An exotherm heat of mixing indicates a high probability that a miscible blend will be obtained.

Examples of hydrophobic polymers useful in the present invention include phenoxy resins such as copolymers of bisphenol A and epichlorohydrin, commercially available from, e.g. Union Carbide Corporation under the tradename Bakelite Phenoxy Resin. These polymers have the following formula:

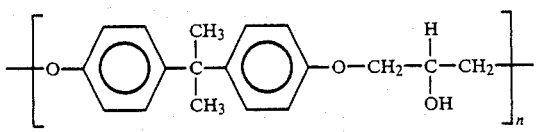

wherein n≃82 to 123 for the resins designated phenoxy resins PKHJ, PKHH, PKHC and PKHA.

Other suitable hydrophobic polymers are copolymers of disulfonyl chloride, diphenyl ether and biphenyl which provide polymers of the formula—$(SO_2\text{-}\phi\text{-}O\text{-}\phi\text{-}SO_2\text{-}\phi\text{-}\phi)\text{+}(SO_2\text{-}\phi\text{-}O\text{-}\phi\text{-}SO_2\text{-}\phi\text{-}O\text{-}\phi)$- and polysulfone resins such as copolymers of bisphenol A and dichlorodiphenylsulfone which are commercially available from Union Carbide Corporation under the tradename Udel Polysulfone Resin. Yet other suitable hydrophobic polymers are the cellulose acetate polymers such as those commercially available from Eastman Kodak Company as cellulose diacetate flake resin. Still other suitable hydrophobic polymers are the polycarbonate polymers such as those formed from bisphenol A carbonate and commercially available from General Electric Company as Lexan ® Polycarbonate Resin.

Still other hydrophobic polymers are useful in the present invention. They include fluorinated polymers such as polyvinylidene fluoride, copolymers of hexafluoropropene and vinylidene fluoride known as Fluorel ® brand polymers and the like; aromatic polyimides such as Upjohn 2080 available from the Upjohn Company and XU-218 available from Ciba Geigy; polymethyl methacrylate; polybenzylmethacrylate (available from Scientific Polymer Products, Inc. (SPP), polyphenylene ether sulfone (available from SPP); copolymers of polyvinyl chloride and vinyl acetate; aromatic polyesters such as PE-100 from Goodyear Chemicals; polyphenylmethacrylate (available from SPP); polyvinylcinnamate (available from SPP); and polyvinylbutyral (available from SPP).

Examples of hydrophilic polymers useful in the present invention include polymers prepared from N-vinyl pyrrolidone, N,N-dimethylacrylamide, polyvinyl methyl ether, N-vinylacetamide, poly-ethyl oxazoline (available from Dow Chemical Company) and the like. Poly-ethyl oxazoline may be prepared by the polymerization of ethyl oxazoline or by the acylation of polyethyleneimine.

The polymer blends of the present invention may be readily prepared by, for example, dissolving the hydrophobic polymer in the monomer of the hydrophilic polymer and then polymerizing the hydrophilic monomer. The hydrophilic monomer is preferably free of polymerization inhibitor. A free radical polymerization initiator is preferably added to the mixture. Polymerization is carried out by providing an activating enegy such as is conventionally used in the polymerization of ethylenically unsaturated monomers. Such energy may include, for example, ultraviolet light, thermal energy, etc.

Polymerization may be carried out in bulk in a conventional manner. When the activating energy is ultraviolet light, the irradiation is typically carried out at a temperature of about 0° to 100° C. for 0.5 minute to 5 hours or more. Following ultraviolet irradiation, the composition may be heated at 50° to 100° C. to complete the polymerization, provided the free radical initiator is thermally activatable.

When the activating energy is heat, polymerization may be carried out at a temperature from about 20° C. to 140° C. for about 5 to 50 hours. The polymerization may also be carried out in stages. Thus, in a first stage, the composition may be heated at 40° to 60° C. for about 5 to 25 hours, and in a second stage it may be heated at 50° to 100° C. for 5 to 25 hours. It is to be understood, of course, that the polymerization conditions are not limited to such temperature and time conditions nor to the use of ultraviolet light or heat as the initiating energy.

Photoinitiators which may be employed to initiate polymerization include those which are well known. See, for example, Chapter II of "Photochemistry" by Calvert and Pitts, John Wiley & Sons (1966). Representative examples of such initiators include acyloin and derivatives thereof, such as benzoin, benzoin methyl ether, benzoin ethyl ether, benzoin isopropyl ether, benzoin isobutyl ether and -methylbenzoin; diketones such as benzil and diacetyl, etc.; ketones such as acetophenone, $\alpha,\alpha,\alpha$-trichloroacetophenone, $\alpha,\alpha,\alpha$-triboroacetophenone, $\alpha,\alpha$-diethoxyacetophenone (DEAP), 2-hydroxy-2-methyl-1-phenyl-1-propanone, o-nitro-$\alpha,\alpha,\alpha$-tribromoacetophenone, benzophenone and p,p'-tetramethyldiaminobenzophenone; $\alpha$-acyloxime esters such as benzil-(0-ethoxycarbonyl)-$\alpha$-monoxime; ketone/amine combinations such as benzophenone/N-methyldiethanolamine, benzophenone/tributylamine and benzophenone/Michler's ketone; and benzilketals such as benzildiethylketal and 2,5-dichlorobenzildimethylketal. Normally, the photoinitiator is used in amounts ranging from about 0.01 to 5% by weight of the total oligomeric composition. When the quantity is less that 0.01% by weight, the photopolymerization rate becomes extremely low. If the photoinitiator is used in excess of 5% by weight, no correspondingly improved effect is observed. Preferably, about 0.1 to 1.0% of photoinitiator is used in the polymerizable compositions.

Examples of useful thermally activated free-radical initiators are the organic peroxides, hydroperoxides, and azo compounds. Such initiators include benzoyl peroxide, tertiary-butyl perbenzoate, diisopropyl peroxydicarbonate, cumene hydroperoxide, azobis(isobutyronitrile), methyl tricapryl ammonium persulfate, and diacyl peroxides such as decanoyl peroxide and the like. Generally, from about 0.1 to 5 percent by weight of thermal initiator is used.

The blends of the invention may also be obtained by dissolving both polymeric components in a suitable solvent (e.g., benzyl alcohol, N,N-dimethyl acetamide, nitromethane, etc.), casting a film of the solution and evaporating the solvent.

The blends of the invention may also be prepared by heating a mixture of the hydrophobic polymer and the hydrophilic polymer to a temperature sufficient to soften the polymers and permit them to be blended together by suitable mechanical mixing.

The preferred polymer blends of the invention are best suited for preparing ophthalmic devices such as corneal transplants, corneal implants, intraocular lenses and soft contact lenses. These blends have good oxygen permeability, good flexibility, good optical clarity, and good mechanical strength.

The ophthalmic devices of the present invention preferably exhibit an oxygen permeability of at least 10 Barrers when measured in accordance with the polarographic oxygen electrode method described by M. F. Refojo et al, "Permeability of Dissolved Oxygen Through Contact Lenses- 1. Cellulose Acetate Butyrate", *Cont. Intraocular Lens Med. J.* 3(4), 27 (1977). More preferably they exhibit an oxygen permeability of at least 20 Barrers.

In order to provide ophthalmic devices such as contact lenses with the most ideal properties, it is desired that the devices be capable of surviving sterilization in a steam autoclave at 120° to 130° C. and/or thermal disinfection at 80° to 100° C.

Shaped articles, such as ophthalmic devices, may be provided by supplying a mold of the desired configuration, charging a mixture of the hydrophilic monomer and hydrophobic polymer thereto and causing polymerization to take place therein. Devices having the desired final configuration may be obtained in this manner. The resultant devices may, however, be machined and/or polished if desired using techniques known to the art.

The non-hydrated monomer-polymer mixture may also be bulk polymerized and the resulting polymer mass may be melt processed in a heated mold to impart the desired shape, as for example in a mold designed to form a contact lens by melt forming of a thermoplastic material. Alternatively, the bulk polymerized material may be machined to impart the desired shape. Solvent cast films may be utilized to form articles of a desired shape by melt processing the cast film (or multiple layers thereof).

Surprisingly, hydrogel articles with excellent mechanical properties may be prepared from the compositions of the invention without employing crosslinking methods. Previously it had been thought necessary to crosslink polymers to achieve good mechanical properties. However, the blend of non-crosslinked polymers of the invention is thermoplastic in character. This provides a great advantage in utility over conventional crosslinked hydrogel polymers since efficient thermal processes may be used to prepare desired hydrogel articles instead of the very inefficient and costly lathe cutting, machining, grinding, and polishing techniques required in the preparation of articles from crosslinked polymers which are inherently not thermally processable.

The following examples are provided to further illustrate the present invention. In the example, all parts given are parts by weight unless otherwise noted.

EXAMPLE 1

Compositions of non-crosslinked polymers were prepared by forming a solution of various water-insoluble, hydrophobic polymers in inhibitor-free N-vinylpyrrolidone monomer (a monomer from which a hydrophilic polymer is obtained). Azo-bis-isobutyronitrile was added to the solutions at a level of 1 part per 100 parts of the polymer and monomer. The various formulations prepared are set out in Table 1.

TABLE 1

| SAMPLE | HYDROPHOBIC POLYMER | HYDROPHOBIC/HYDROPHILIC PARTS |
|---|---|---|
| A | 1 | 20/80 |
| B | 1 | 15/85 |
| C | 1 | 13/87 |
| D | 1 | 10/90 |
| E | 2 | 15/85 |
| F | 2 | 10/90 |
| G | 3 | 20/80 |
| H | 4 | 20/80 |
| I | 3 | 15/85 |
| J | 3 | 10/90 |
| K | 4 | 10/90 |
| L | 3 | 5/95 |
| M | 5 | 20/80 |
| N | 6 | 10/90 |
| O | 7 | 10/90 |
| P | 8 | 10/90 |

1. Phenoxy Resin PKHJ, available from Union Carbide Corporation.
2. Phenoxy Resin PKHA, available from Union Carbide Corporation.
3. Udel P-3500 available from Union Carbide Corporation.
4. Udel P-1700 available from Union Carbide Corporation.
5. Cellulose acetate having the structural formula

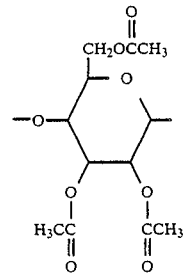

and having a degree of substitution of 2.3 wherein the primary hydroxy group is partially unsubstituted.

6. Polymethyl methacrylate.
7. Polycarbonate having the formula

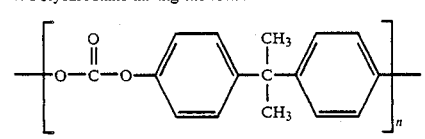

8. VMCH available from Union Carbide Corporation and having the formula

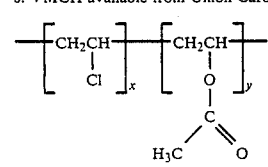

The solutions were degassed under vacuum. Samples of each solution were placed between spaced glass plates. The resultant assemblies were placed in an oven maintained at 55° C. overnight (approximately 16 hours). The assemblies were then removed from the oven, cooled and the samples removed and air dried. Samples were then fully hydrated by immersion in excess water for at least two hours at room temperature. Various characteristics of the samples were then determined. The results are set out in Table 2.

| SAMPLE | WATER ABSORPTION (%) | O₂ PERMEABILITY (Barrers) | TENSILE STRENGTH (Kg/cm²) | % ELONG. | MODULUS | GLASS TRANS. TEMP. (DRY SAMPLE) ($T_g$ °C.) |
|---|---|---|---|---|---|---|
| A | 69 | 27 | 14.8 | 183 | 25.8 | 121 |
| B | 75 | 32 | 7.6 | 123 | 12.6 | — |
| C | 77 | 32 | 7.3 | 160 | 10.9 | 121 |
| D | 83 | 41 | 3.1 | 110 | 3.0 | 116 |
| E | 77 | 35 | 7.3 | 90 | 15.9 | — |
| F | 84 | 44 | 2.6 | 80 | 5.1 | — |
| G | 57 | 16 | 31.9 | 175 | 59.2 | 134 |
| H | 57 | 19 | 31.2 | 170 | 63.2 | — |
| I | 64 | 22 | 19.6 | 175 | 30.6 | 132 |
| J | 73 | 32 | 9.3–12.3 | 190–255 | 13.8–14.5 | 132 |
| K | 73 | 30 | 8.7–10.9 | 190–240 | 10.2–13.8 | — |
| L | 82 | 37 | 2.8 | 195 | 3.5 | 145 |
| M | 75 | 30 | 11.9 | 75 | 64.3 | 136 |
| N | 85 | 49 | 1.1 | 85 | 1.7 | 115 |
| O | 89 | 65 | 0.2 | 115 | 0.4 | 140 |
| P | — | — | — | — | — | 97 |

EXAMPLE 2

Poly(vinylidene fluoride) (1.0 g., Solef 1008, Solvay Chemical Company) was dissolved in N-vinylpyrrolidone monomer (9.0 g) by stirring while heating at approximately 130° C. until a clear solution was obtained. A benzoin photoinitiator (10 mg, 0.1% Darocure 1173 Merck Chemical Co.) was added and the warm solution was placed in a mold constructed from two glass plates and a Teflon spacer gasket of approximately 0.2 mm thickness. Irradiation for approximately one hour with an ultraviolet lamp (G.E. Sunlamp, 275 watt) resulted in complete polymerization to a transparent, tough film which when placed in water became a water-swollen hydrogel film of good clarity and strength, having 89% weight water.

EXAMPLE 3

A solution of poly(vinylidene fluoride) in monomeric N-vinyl pyrrolidone (10/90 ratio) was prepared as above described in Example 2. A thermally-sensitive free radical initiator (azo bis-isobutyronitrile) was dissolved in the solution at room temperature at the 0.5 weight percent level. The solution of monomer, polymer, and initiator was placed in an oven at approximately 55° C. for 16 hours. Complete polymerization occurred to give a strong transparent film which when swollen in water provided a clear, strong hydrogel of approximately 80 weight percent water content.

EXAMPLE 4

Compositions of powdered poly-N-vinylpyrrolidone (Aldrich Chemical Co., molecular weight 40,000) and powdered Phenoxy ® resin (Union Carbide Corporation, Phenoxy PKHJ resin) were mixed by tumbling in a container. The mixture of powders was placed in a Brabender melt mixer, heated at 175° C. and mixed for approximately six minutes, until a homogeneous melt was obtained. The product was cooled and removed. Small samples of each composition were melt-pressed in a hot hydraulic press heated to 175° C. to obtain pressed film samples of approximately 0.5 mm thickness. The pressed samples were strong and transparent and when examined for water absorption for utility as hydrogels, the following results were obtained:

TABLE 3

| SAMPLE NO. | PARTS BY WT. PNVP (hydrophilic) polymer) | PARTS BY WEIGHT PHENOXY RESIN (hydrophobic) polymer) | WT. % H₂O |
|---|---|---|---|
| A | 40 | 60 | 19 |
| B | 50 | 50 | 32 |
| C | 60 | 40 | 45 |
| D | 70 | 30 | 55 |
| E | 80 | 20 | 69 |
| F | 85 | 15 | 75 |
| G | 90 | 10 | 83 |

EXAMPLE 5

Monomeric N,N-dimethylacrylamide (10 parts) and various water-insoluble polymers (90 parts) were mixed at approximately 50° C. for several hours in order to form solutions of polymer. The solubility parameter of poly-N, N-dimethylacrylamide is approximately 10.3 (cal/cm³)$^{1/2}$. Those combination giving clear solutions were subjected to ultraviolet light-induced polymerization using a benzoin photoinitiator (Darocure 1173, Merck Chemical Company) at the 0.5 weight percent level. Table 4 shows that only those water-insoluble polymers within a narrow solubility parameter range were observed to give miscible polymer blend hydrogels.

TABLE 4

| | | WATER-INSOLUBLE POLYMER | | |
|---|---|---|---|---|
| EXAMPLE NO. | TYPE | SOLUBILITY PARAMETER (cal/cm³)$^{\frac{1}{2}}$ | SOLUTION OBSERVED | PHOTOPOLYMERIZATION RESULT |
| A | Sulfone 35 | 11–11.6 | Clear | Opaque, 2-phase mixture |
| B | PMMA | 9.2 | Clear | Semi-opaque, 2-phase mixture |
| C | Phenoxy J | 10.7 | Clear | Clear transparent blend* |

TABLE 4-continued

| | WATER-INSOLUBLE POLYMER | | | |
|---|---|---|---|---|
| EXAMPLE NO. | TYPE | SOLUBILITY PARAMETER $(cal/cm^3)^{\frac{1}{2}}$ | SOLUTION OBSERVED | PHOTOPOLYMERIZATION RESULT |
| D | Polycarbonate | 9.6 | Insoluble | — |
| E | Cellulose Acetate | 10.2 | Clear | Clear transparent blend |
| F | Polystyrene | 9.05 | Clear | Opaque, 2-phase mixture |
| G | Polyvinyl Acetate | 8.8 | Clear | Opaque, 2-phase mixture |
| H | Polybutadiene | 8.3 | Insoluble | — |

*Melt pressing at 175° C. gave a transparent film which swelled without dissolving in water.

EXAMPLE 6

A series of miscible blends of cellulose acetate (CA), acetate content 2.3 acetates per anhydroglucose ring, with poly N-vinylpyrrolidone (PNVP) were prepared covering the composition range from 0% cellulose acetate to 100% cellulose acetate by 10% increments. The appropriate amount of each polymer was weighed into a container, solvent (N,N-dimethylacetamide) was added in amount sufficient to provide mixtures of 90% solvent and 10% polymer solids, and film samples were prepared by evaporation of solvent. Final drying was done in a vacuum oven at elevated temperature (120°–130° C.). Film samples were fully hydrated by soaking in distilled water overnight and properties were determined which included % water uptake, refractive index, oxygen permeability, ultimate tensile strength, elongation at break, and Young's modulus as summarized in the following table:

| Sample No. | % PNVP | % CA | Wt. % $H^2O$ | Refr. Index | Oxygen Perm. | Tensile Strength $(kg/cm^2)$ | % Elong. | Modulus $(kg/cm^2)$ |
|---|---|---|---|---|---|---|---|---|
| A | 100 | 0 | Soluble | — | — | — | — | — |
| B | 90 | 10 | 89.2 | 1.336 | 33.0 | 2.0 | 91 | 3.4 |
| C | 80 | 20 | 79.7 | 1.352 | 25.2 | 7.7 | 112 | 12.7 |
| D | 70 | 30 | 70.1 | 1.369 | 19.5 | 23.2 | 142 | 35.6 |
| E | 60 | 40 | 61.1 | 1.407 | 17.6 | 38.2 | 153 | 62.0 |
| F | 50 | 50 | 50.5 | 1.424 | 12.7 | 70.8 | 152 | 110.7 |
| G | 40 | 60 | 42.6 | 1.437 | 8.6 | 103.9 | 176 | 185.0 |
| H | 30 | 70 | 33.8 | 1.446 | 5.9 | 111.9 | 147 | 352.6 |
| I | 20 | 80 | 25.1 | 1.470 | 3.5 | 105.3 | 80 | 510.8 |
| J | 10 | 90 | 20.2 | 1.487 | 2.4 | 95.5 | 66 | 447.3 |
| K | 0 | 100 | 14.1 | 1.468 | 1.9 | 42.1 | 49 | 278.1 |

Sample C was formed into a contact lense. Samples B and D–J could also be formed into contact lenses.

EXAMPLE 7

A sample of Phenoxy ® PKHJ Resin/PNVP blend was prepared by free radical polymerization of a solution of 9.8 parts of N-vinyl pyrrolidone and 0.2 parts by Phenoxy ® PKHJ Resin by the method of Example 2. The transparent blend product was placed in a large volume of distilled water for swelling overnight and underwent water swell to a very soft highly-swollen transparent hydrogel which was not soluble in the excess water present. The water content of this hydrogel was in excess of 95 weight percent water. The anhydrous blend could be processed into a variety of shpes including contact lenses, corneal implants, corneal transplants and intraocular lenses.

EXAMPLE 8

Example 5 was repeated using 5 parts of monomeric N,N-dimethyl-acrylamide and 95 parts of Phenoxy ® PKHJ. A miscible blend hydrogel product was obtained which could be processed into various ophthalmic devices.

EXAMPLE 9

A series of miscible blends of 80 parts by weight PNVP and 20 parts by weight of various hydrophobic polymers was prepared. The hydrophobic polymers employed were:

A. Aromatic polyimide (available from Upjohn Company as Upjohn 2080).

B. Aromatic polyimide (available from Ciba Geigy as XU 218).

C. Polybenzylmethacrylate (available from Scientific Polymer Products, Inc.)

D. Polyphenylene ether sulfone (available from Scientific Polymer Products, Inc.).

The blends were prepared by solvent-casting a film from solutions of the polymer components in N,N-dimethylacetamide or N,N-dimethyl formamide. All gave transparent xerogels with a single glass transition temperature as measured by differential scanning calorimetry (DSC) and all gave strong transparent hydrogels when swollen in water. All could be processed into opticl articles.

EXAMPLE 10

Blends containing 50 parts by weight PNVP and 50 parts by weight of one of the following hydrophobic polymers were prepared:

A. PE100 Aromatic polyester, Goodyear, a polyester prepared from a mixture of terephthalic and isophthalic acids.

B. Polyphenylmethacrylate - Scientific Polymer Products, Inc.

C. Polyvinylcinnamate - Scientific Polymer Products, Inc.

D. Polyvinylbutyral - Scientific Polymer Products, Inc.

The blends were prepared as described in Example 10 and gave transparent xerogels with a single glass transition temperature as measured by DSC and all gave strong transparent hydrogels when swollen in water. All could be processed into optical articles.

EXAMPLE 11

A miscible blend was prepared using poly-ethyl oxazoline (sold by Dow Chemicaal Co.) as the hydrophilic component and Phenoxy ® PKHJ Resin as the hydrophobic component. The materials were mixed in a weight ratio of 80/20 hydrophilic/hydrophobic and solvent cast to form a miscible blend. The blend was dried at 130° C. and was transparent. It showed a single glass transition temperature, and when hydrated in distilled water gave a flexible, strong, transparent hydrogel product.

What is claimed is:

1. An ophthalmic device comprising a miscible blend of non-crosslinked polymers comprising from about 2 to 95 parts by weight of a water-insoluble, hydrophobic polymer and from about 98 to 5 parts by weight of a hydrophilic polymer, wherein said hydrophobic and hydrophilic polymers are not covalently bonded to each other, said blend being transparent and capable of absorbing a sufficient quantity of water to provide a hydrated material containing at least 50% by weight water.

2. An ophthalmic device according to claim 1 selected from contact lenses, corneal implants, corneal transplants, and intraocular lenses.

3. An ophthalmic device according to claim 1 comprising from about 10 to 30 parts by weight hydrophobic polymer and from about 90 to 70 parts by weight hydrophilic polymer.

4. An ophthalmic device according to claim 1 comprising from about 10 to 20 parts by weight of said hydrophobic polymer and from about 90 to 80 parts by weight of said hydrophilic polymer.

5. An ophthalmic device according to claim 1 wherein said hydrophobic polymer is selected form copolymers of bisphenol A and epichlorohydrin, copolymers of disulfonyl chloride, diphenyl ether and biphenyl, copolymers of bisphenol A and dichlorodiphenylsulfone, aromatic polyimides, aromatic polyesters, cellulose acetate polymers, polycarbonate polymers, polyvinylidene fluoride, copolymers of hexafluoropropene and vinylidene fluoride, polymethylmethacrylate, polybenzylmethacrylate, polyphenylmethacrylate, polyvinyl cinnamate, polyvinylbutyral, polyphenylene ether sulfone, and copolymers of polyvinyl chloride and vinyl acetate.

6. An ophthalmic device according to claim 1 wherein said hydrophilic polymer is selected from polyvinyl methyl ether, polyethyl oxazoline, polymers prepared from N-vinyl pyrrolidone polymers prepared from N,N-dimethylacrylamide and polymers prepared from N-vinylacetamide.

7. An ophthalmic device according to claim 6 wherein said hydrophilic polymer is prepared from N-vinylpyrrolidone.

8. A contact lens according to claim 7 wherein said hydrophobic polymer is selected from copolymers of bisphenol A and epichlorohydrin, copolymers of disulfonyl chloride, diphenyl ether and biphenyl, copolymers of bisphenol A and dichlorodiphenylsulfone, aromatic polyimides, aromatic polyesters, cellulose acetate polymers, polycarbonate polymers, polyvinylidene fluoride, copolymers of hexafluoropropene and vinylidene fluoride, polymethylmethacrylate, polybenzylmethacrylate, polyphenylmethacrylate, polyvinyl cinnamate, polyvinylbutyral, polyphenylene ether sulfone, and copolymers of polyvinyl chloride and vinyl acetate.

9. A contact lens according to claim 2.

10. A corneal implant according to claim 2.

11. A corneal transplant according to claim 2.

12. An intraocular lens according to claim 2.

13. A process for thermally processing a miscible blend of polymer comprising the steps of providing a miscible blend of non-crosslinked polymers comprising from about 2 to 95 parts by weight of a water-insoluble, hydrophobic polymer and from about 98 to 5 parts by weight of a hydrophilic polymer, wherein said hydrophobic and hydrophilic polymers are not covalently bonded to each other, said blend being transparent and capable of absorbing a sufficient quantity of water to provide a hydrated material containing at least 50% by weight water, providing a mold having the desired configuration, charging said blend to said mold, and heating said blend to a temperature sufficient to cause melt flow of said blend.

* * * * *

UNITED STATES PATENT AND TRADEMARK OFFICE
CERTIFICATE OF CORRECTION

PATENT NO. : 4,859,719

DATED : AUGUST 22, 1989

INVENTOR(S) : RONALD F. OFSTEAD

It is certified that error appears in the above-identified patent and that said Letters Patent is hereby corrected as shown below:

Column 1, line 57 "coompositions" should be

--compositions --.

Column 2, line 56 "neight" should be --neither--.

Column 6, line 30 "triboroacetophenone" should be

--tribromoacetophenone--.

Column 11, line 61 "shpes" should be --shapes--.

Signed and Sealed this

Fourth Day of September, 1990

Attest:

HARRY F. MANBECK, JR.

*Attesting Officer*     *Commissioner of Patents and Trademarks*